US006822242B2

United States Patent
Ikami

(10) Patent No.: US 6,822,242 B2
(45) Date of Patent: Nov. 23, 2004

(54) IMAGE DATA PRODUCING METHOD AND APPARATUS

(75) Inventor: Seishi Ikami, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 310 days.

(21) Appl. No.: 09/988,370

(22) Filed: Nov. 19, 2001

(65) Prior Publication Data

US 2002/0060295 A1 May 23, 2002

(30) Foreign Application Priority Data

Nov. 20, 2000 (JP) ...................................... 2000-353093

(51) Int. Cl.[7] .............................................. G01N 21/64
(52) U.S. Cl. .................................. 250/458.1; 250/461.1
(58) Field of Search ........................... 250/458.1, 459.1, 250/461.1, 461.2

(56) References Cited

U.S. PATENT DOCUMENTS

| | | | | |
|---|---|---|---|---|
| 4,954,714 A | * | 9/1990 | Pollak et al. ............. | 250/458.1 |
| 5,430,813 A | * | 7/1995 | Anderson et al. ............. | 385/12 |
| 5,891,656 A | * | 4/1999 | Zarling et al. ............... | 435/792 |
| 5,936,731 A | * | 8/1999 | Cabib et al. ................. | 356/346 |
| 6,040,940 A | * | 3/2000 | Kawasaki .................... | 359/389 |

FOREIGN PATENT DOCUMENTS

| | | |
|---|---|---|
| JP | 64-60782 | 3/1989 |
| JP | 64-60784 | 3/1989 |
| JP | 4-3952 | 1/1992 |

* cited by examiner

Primary Examiner—Constantine Hannaher
Assistant Examiner—Timothy J. Moran
(74) Attorney, Agent, or Firm—Sughrue Mion, PLLC

(57) ABSTRACT

An image data producing apparatus includes comprising at least one stimulating ray source for emitting a stimulating ray, a stage on which an image carrier including independently formed and two-dimensionally distributed specimen spots, at least some of which contain a fluorescent substance, is to be placed, a two-dimensional area sensor, and a controller for irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens. According to the thus constituted image data producing apparatus, it is possible to produce low-noise image data rapidly with a simple operation by irradiating the image carrier including independently formed and two-dimensionally distributed specimen spots with a stimulating ray to excite the fluorescent substance and photoelectrically detecting fluorescence emission released from the fluorescent substance.

25 Claims, 9 Drawing Sheets

IMAGE DATA PRODUCING METHOD AND APPARATUS

BACKGROUND OF THE INVENTION

The present invention relates to an image data producing method and apparatus and, particularly, to such an image data producing method and apparatus which can produce low-noise image data rapidly with a simple operation by irradiating an image carrier including independently formed and two-dimensionally distributed specimen spots, at least some of which contain a fluorescent substance, with a stimulating ray to excite the fluorescent substance and photoelectrically detecting fluorescence emission released from the fluorescent substance.

DESCRIPTION OF THE PRIOR ART

An autoradiographic system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactive labeling substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

Unlike the system using a photographic film, according to the autoradiographic system using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence detecting system using a fluorescent substance as a labeling substance instead of a radioactive labeling substance in the autoradiographic system is known. According to this system, it is possible to study a genetic sequence, to study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Furthermore, an analysis plate, called a micro-titer plate, that is provided with numerous wells in which a specimen solution can be held is known to be used with one fluorescence detecting system. According to this system, biochemical analysis is effected by accommodating a specimen solution labeled with a fluorescent substance in wells, irradiating the specimen solution with a stimulating ray to excite the fluorescent substance and detecting fluorescence emission released from the fluorescent substance.

Further, a micro-array detecting system has been recently developed, which comprises the steps of using a spotting device to drop at different positions on the surface of a carrier such as a slide glass plate, a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emitted from a labeling substance such as a fluorescent substance, dye or the like, and analyzing the substance derived from a living organism. This micro-array image detecting system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In the fluorescent detecting system and the micro-array detecting system, data for biochemical analysis such as image data are produced by irradiating a labeling substance with a stimulating ray to excite it and photoelectrically detecting fluorescence emission released from the labeling substance by a light detector. Therefore, since noise is generated to lower the accuracy of analysis if the stimulating ray enters the light detector, a stimulating ray cut filter is provided for blocking the stimulating ray and preventing it from entering the light detector.

However, even when a stimulating ray cut filter is provided, it is difficult to completely block the stimulating ray. Therefore, it has been proposed to lower noise caused by detecting the stimulating ray by stopping the irradiation with the stimulating ray after irradiating a labeling substance with the stimulating ray to excite the labeling substance and detecting residual fluorescence emission released from the labeling substance even after the completion of the irradiation with the stimulating ray.

In the case of using this method, residual fluorescence emission is detected by irradiating a fluorescent substance contained in a specimen solution held in a number of wells of a micro-titer plate, biochemical analysis data are conventionally produced by sequentially irradiating the wells with a stimulating ray to excite the fluorescent substance contained in the specimen solution in the wells and residual fluorescence emission released from the fluorescent substance after stopping the irradiation with the stimulating ray is photoelectrically detected using a light detector such as a photomultiplier.

However, since the micro-titer plate is formed with numerous wells, e.g., 96 wells, and the amount of residual fluorescence emission detected by one-time irradiation with the stimulating ray is small, it is necessary to repeat an operation comprising the steps of irradiation with the stimulating ray, stopping the irradiation with the stimulating ray and detecting residual fluorescence emission. Therefore, it inevitably takes a long time to irradiate the fluorescent substance contained in the specimen solution in all wells, photoelectrically detect residual fluorescence emission substance using a light detector such as a photomultiplier and produce biochemical analysis data. As a result, the progress of reaction of the specimen solution in the wells becomes different between the individual wells.

In order to solve this problem, biochemical analysis data are conventionally produced by stimulating the fluorescent substance contained in a specimen solution in a well and photoelectrically detecting residual fluorescence emission from the substance using a light detector such as a photomultiplier, each time the specimen solution is poured into a well.

However, it is not only troublesome to produce biochemical analysis data in this manner but also time-consuming and uneconomical.

In the micro-array detecting system, the state of spots obtained by spotting specific binding substances onto the surface of a substrate such as a slide glass plate or a membrane filter and hybridizing a substance derived from a living organism and labeled with a labeling substance with them may change with the elapse of time and, therefore, there may arise similar problems to those in the micro-titer plate.

SUMMARY OF THE INVENTION

It is therefore an object of the present invention to provide an image data producing method and apparatus which can produce low-noise image data rapidly with a simple operation by irradiating an image carrier including independently formed and two-dimensionally distributed specimen spots, at least some of which contain a fluorescent substance, with a stimulating ray to excite the fluorescent substance and photoelectrically detecting fluorescence emission released from the fluorescent substance.

The above and other objects of the present invention can be accomplished by an image data producing method comprising the steps of irradiating an image carrier including independently formed and two-dimensionally distributed specimen spots, at least some of which contain a fluorescent substance, with a stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using a two-dimensional area sensor.

According to the present invention, since image data are produced by irradiating an image carrier with a stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using a two-dimensional area sensor, the image carrier is not irradiated with the stimulating ray while the two-dimensional area sensor detects the residual fluorescence emission and, therefore, it is possible to markedly lower noise in image data caused by detecting the stimulating ray by the two-dimensional area sensor.

In a preferred aspect of the present invention, the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are repeated two or more times.

According to this preferred aspect of the present invention, since the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are repeated two or more times, a sufficient amount of the residual fluorescence emission can be detected by the two-dimensional area sensor and, therefore, image data capable of generating a desired image can be produced.

In a further preferred aspect of the present invention, the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on and off operations of at least one stimulating ray source for emitting a stimulating ray and opening and closing operations of a shutter of the two-dimensional area sensor.

According to this preferred aspect of the present invention, since the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on and off operations of at least one stimulating ray source for emitting a stimulating ray and opening and closing operations of a shutter of the two-dimensional area sensor, residual fluorescence emission can be reliably detected by the two-dimensional area sensor only when the image carrier is not irradiated with the stimulating ray and, therefore, it is possible to markedly lower noise in image data caused by detecting the stimulating ray by the two-dimensional area sensor.

In another preferred aspect of the present invention, the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on-off operations of at least one stimulating ray source for emitting a stimulating ray and opening and closing operations of a shutter of the two-dimensional area sensor using a chopper.

According to this preferred aspect of the present invention, since the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on-off operations of at least one stimulating ray source for emitting a stimulating ray and opening and closing operations of a shutter of the two-dimensional area sensor using a chopper, residual fluorescence emission can be reliably detected by the two-dimensional area sensor only when the image carrier is not irradiated with the stimulating ray and, therefore, it is possible to markedly lower noise in image data caused by detecting the stimulating ray by the two-dimensional area sensor.

In a further preferred aspect of the present invention, image data are produced by detecting residual fluorescence emission by the two-dimensional area sensor via a filter for cutting at least light having a wavelength of the stimulating ray.

According to this preferred aspect of the present invention, since residual fluorescence emission is detected by the two-dimensional area sensor via the filter for cutting at least light having a wavelength of the stimulating ray, even if the stimulating ray is present for some reason in an apparatus when residual fluorescence emission is detected by the two-dimensional area sensor, it is possible to reliably prevent the stimulating ray from being detected by the two-dimensional area sensor and, therefore, it is possible to markedly lower noise in image data caused by detecting the stimulating ray by the two-dimensional area sensor.

In a further preferred aspect of the present invention, image data are produced by detecting residual fluorescence emission by the two-dimensional area sensor via a Fresnel lens.

According to this preferred aspect of the present invention, since residual fluorescence emission is detected by the two-dimensional area sensor via the Fresnel lens, in the case where an image of fluorescent dye labeling a specimen solution contained in a number of wells of the microtiter plate is read out, image data can be produced without parallax by detecting fluorescence emission released from the micro-titer plate by the two-dimensional area sensor.

In a further preferred aspect of the present invention, image data are produced by using a CCD camera as the two-dimensional area sensor.

In a further preferred aspect of the present invention, image data are produced by using a cooled CCD camera as the two-dimensional area sensor.

According to this preferred aspect of the present invention, since a cooled CCD camera is used as the two-dimensional area sensor, it is possible to expose the cooled CCD camera for a sufficient long time period and, therefore, even if the residual fluorescence emission is very weak, image data can be produced in a desired manner.

In a further preferred aspect of the present invention, a micro-titer plate formed with numerous wells holding specimens labeled with a fluorescent dye is used as the image carrier.

According to this preferred aspect of the present invention, since image data of the fluorescent dye labeling specimens held in all wells formed in the micro-titer plate can be produced by the two-dimensional area sensor at the same time, it is possible for all wells formed in the micro-titer plate to hold specimens labeled with the fluorescent dye at one time and, therefore, it is possible to produce image data with markedly low noise rapidly with a simple operation.

The above other objects of the present invention can be accomplished by an image data producing apparatus comprising at least one stimulating ray source for emitting a stimulating ray, a stage on which an image carrier including independently formed and two-dimensionally distributed specimen spots, at least some of which contain a fluorescent substance, is to be placed, a two-dimensional area sensor, and a control means for irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens.

According to the present invention, since the image data producing apparatus includes the control means for irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens, the image carrier is not irradiated with the stimulating ray while the two-dimensional area sensor detects residual fluorescence emission and, therefore, it is possible to markedly lower noise in image data caused by detecting the stimulating ray by the two-dimensional area sensor.

In a preferred aspect of the present invention, the control means is constituted so as to repeat the steps of irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens two or more times.

According to this preferred aspect of the present invention, since the steps of irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens are repeated two or more times, a sufficient amount of the residual fluorescence emission can be detected by the two-dimensional area sensor and, therefore, image data capable of generating a desired image can be produced.

In a further preferred aspect of the present invention, the control means is constituted so as to synchronize on and off operations of at least one stimulating ray source and opening and closing operations of a shutter of the two-dimensional area sensor in such a manner that the shutter of the two-dimensional area sensor is closed when the at least one stimulating ray source is held on and it is opened only when the at least one stimulating ray source is held off, thereby irradiating the image carrier placed on the stage with a stimulating ray emitted from the at least one stimulating ray source to excite a fluorescent substance contained in the specimens, stopping the irradiation with the stimulating ray and causing the two-dimensional area sensor to photoelectrically detect residual fluorescence emission released from the fluorescent substance contained in the specimens.

According to this preferred aspect of the present invention, since the control means is constituted so as to synchronize on and off operations of at least one stimulating ray source and opening and closing operations of a shutter of the two-dimensional area sensor in such a manner that the shutter of the two-dimensional area sensor is closed when the at least one stimulating ray source is held on and is opened only when the at least one stimulating ray source is held off, thereby irradiating the image carrier placed on the stage with a stimulating ray emitted from the at least one stimulating ray source to excite a fluorescent substance contained in the specimens, stopping the irradiation with the stimulating ray and causing the two-dimensional area sensor to photoelectrically detect residual fluorescence emission released from the fluorescent substance contained in the specimens, residual fluorescence emission can be reliably detected by the two-dimensional area sensor only when the image carrier is not irradiated with the stimulating ray and, therefore, it is possible to markedly lower noise in image data caused by detecting the stimulating ray by the two-dimensional area sensor.

In another preferred aspect of the present invention, the image data producing apparatus further comprises a disk-like rotatable chopper having at least two openings and the control means is constituted so as to control the rotation of the chopper in such a manner that a light detecting surface of the two-dimensional area sensor is covered by the chopper when one of the openings of the chopper is located in an optical path of the stimulating ray emitted from the at least one stimulating ray source and one of the openings of the chopper is located in front of the light detecting surface of the two-dimensional area sensor only when the chopper is located in the optical path of the stimulating ray emitted from the at least one stimulating ray source to cut the stimulating ray.

According to this preferred aspect of the present invention, since the image data producing apparatus further comprises a disk-like rotatable chopper having at least two openings and the control means is constituted so as to control the rotation of the chopper in such a manner that a light detecting surface of the two-dimensional area sensor is covered by the chopper when one of the openings of the chopper is located in an optical path of the stimulating ray emitted from the at least one stimulating ray source and one of the openings of the chopper is located in front of the light detecting surface of the two-dimensional area sensor only when the chopper is located in the optical path of the stimulating ray emitted from the at least one stimulating ray source to cut the stimulating ray, residual fluorescence emission can be reliably detected by the two-dimensional area sensor only when the image carrier is not irradiated with the stimulating ray and, therefore, it is possible to markedly lower noise in image data caused by detecting the stimulating ray by the two-dimensional area sensor.

In a further preferred aspect of the present invention, the image data producing apparatus further comprises a light guide for leading a stimulating ray emitted from the at least one stimulating ray source and the control means is constituted so as to control the rotation of the chopper in such a manner that a light detecting surface of the two-dimensional area sensor is covered by the chopper when one of the openings of the chopper is located in front of a stimulating ray emitting end portion of the light guide and one of the openings of the chopper is located in front of the light detecting surface of the two-dimensional area sensor only when the chopper is located in front of the stimulating ray emitting end portion of the light guide to cut the stimulating ray.

According to this preferred aspect of the present invention, since the image data producing apparatus further comprises a light guide for leading a stimulating ray emitted from the at least one stimulating ray source, it is possible to efficiently irradiate the image carrier with a stimulating ray emitted from the at least one stimulating ray source.

In a further preferred aspect of the present invention, the light guide is constituted by an optical fiber bundle.

In a further preferred aspect of the present invention, the chopper is formed with four openings.

According to this preferred aspect of the present invention, even when the decay time of residual fluorescence emission released from a fluorescent substance is short, the residual fluorescence emission can be reliably detected by the two-dimensional area sensor without rotating the chopper at an excessively high speed only when the image carrier is not irradiated with the stimulating ray and, therefore, it is possible to markedly lower noise in image data caused by detecting the stimulating ray by the two-dimensional area sensor.

In a further preferred aspect of the present invention, the image data producing apparatus further comprises a filter for cutting at least light having a wavelength of the stimulating ray.

According to this preferred aspect of the present invention, since the image data producing apparatus further comprises a filter for cutting at least light having a wavelength of the stimulating ray, even if the stimulating ray is present for some reason in an apparatus when residual fluorescence emission is detected by the two-dimensional area sensor, it is possible to reliably prevent the stimulating ray from being detected by the two-dimensional area sensor and, therefore, it is possible to markedly lower noise in image data caused by detecting the stimulating ray by the two-dimensional area sensor.

In a further preferred aspect of the present invention, the image data producing apparatus further comprises a Fresnel lens between the stage and the two-dimensional area sensor.

According to this preferred aspect of the present invention, since the image data producing apparatus further comprises a Fresnel lens between the stage and the two-dimensional area sensor, in the case where an image of fluorescent dye labeling a specimen solution contained in a number of wells of the micro-titer plate is read out, image data can be produced without parallax by detecting fluorescence emission released from the micro-titer plate by the two-dimensional area sensor.

In a further preferred aspect of the present invention, the two-dimensional area sensor is constituted as a CCD camera.

In a further preferred aspect of the present invention, the two-dimensional area sensor is constituted as a cooled CCD camera.

According to this preferred aspect of the present invention, since the two-dimensional area sensor is constituted as a cooled CCD camera, it is possible to expose the cooled CCD camera for a sufficient long time period and, therefore, even if the residual fluorescence emission is very weak, image data can be produced in a desired manner.

In a further preferred aspect of the present invention, the image carrier is constituted by a micro-titer plate formed with numerous wells holding specimens labeled with a fluorescent dye.

According to this preferred aspect of the present invention, since image data of the fluorescent dye labeling specimens held in all wells formed in the micro-titer plate can be produced by the two-dimensional area sensor at the same time, it is possible for all wells formed in the micro-titer plate to hold specimens labeled with the fluorescent dye at one time and, therefore, it is possible to produce image data with markedly low noise rapidly with a simple operation.

The above and other objects and features of the present invention will become apparent from the following description made with reference to the accompanying drawings.

DESCRIPTION OF THE PREFERRED EMBODIMENT

Figure 1:
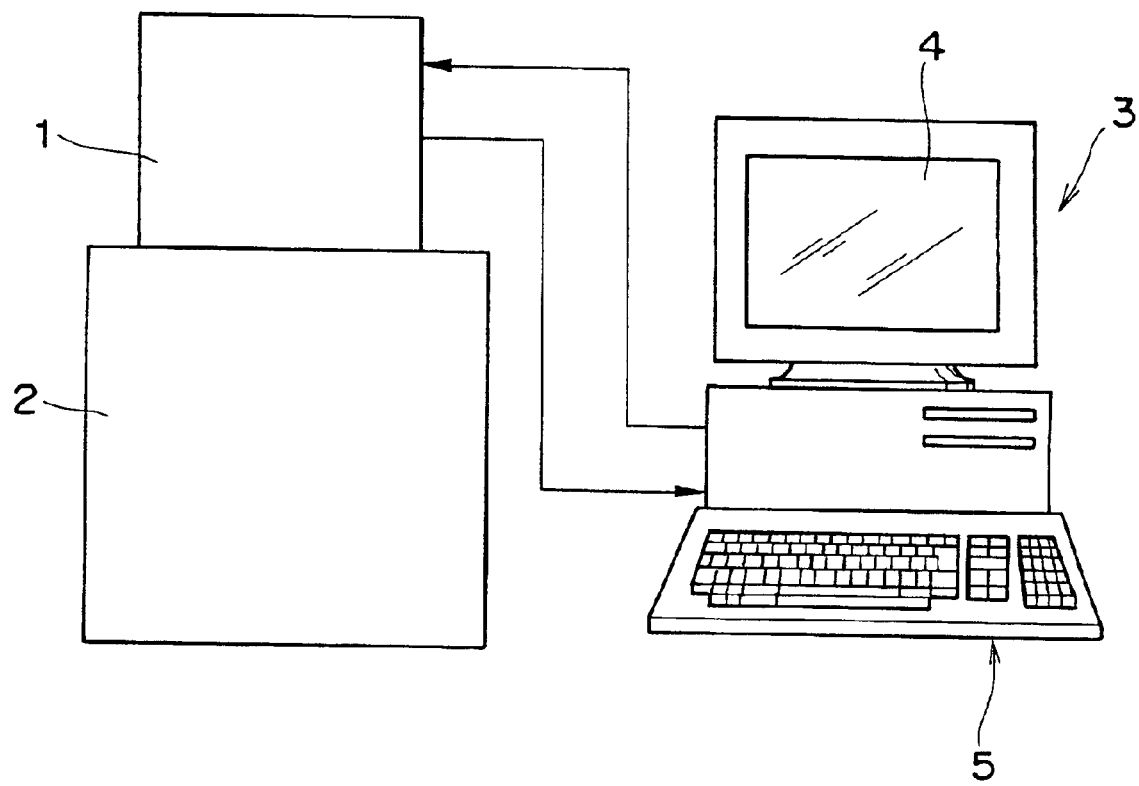
FIG. 1 is a schematic front view showing an image data producing apparatus which is a preferred embodiment of the present invention.

FIG. 1 is a schematic front view showing an image data producing apparatus which is a preferred embodiment of the present invention.

As shown in FIG. 1, the image data producing apparatus includes a cooled CCD camera 1, a dark box 2 and a personal computer 3. As shown in FIG. 1, the personal computer 3 is equipped with a CRT 4 and a keyboard 5.

Figure 2:
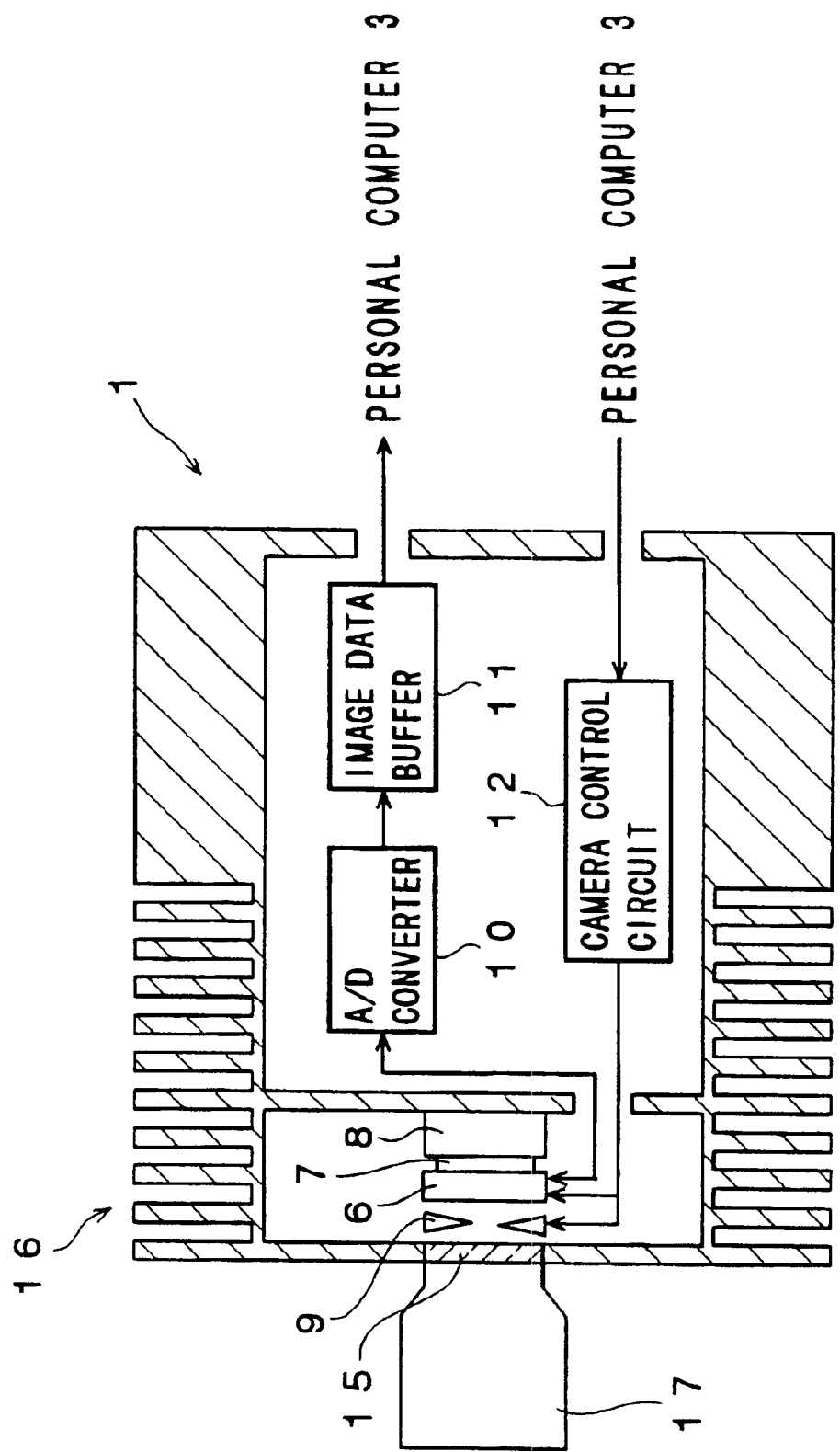
FIG. 2 is a schematic cross sectional view showing a cooled CCD camera.

FIG. 2 is a schematic longitudinal cross sectional view showing the cooled CCD camera 1.

As shown in FIG. 2, the cooled CCD camera 1 includes a CCD 6, a heat transfer plate 7 made of a metal such as aluminum, a Peltier element 8 for cooling the CCD 6, a shutter 9 disposed in front of the CCD 6, an A/D converter 10 for converting analog image data produced by the CCD 6 to digital image data, an image data buffer 11 for temporarily storing the image data digitized by the A/D converter 10, and a camera control circuit 12 for controlling the operation of the cooled CCD camera 1. An opening formed between the dark box 2 and the cooled CCD camera 1 is closed by a glass plate 15 and the periphery of the cooled CCD camera 1 is formed with heat dispersion fins 16 over substantially half its length for dispersing heat.

A camera lens 17 having a lens focus adjusting function disposed in the dark box 2 is mounted on the front surface of the glass plate 15.

Figure 3:
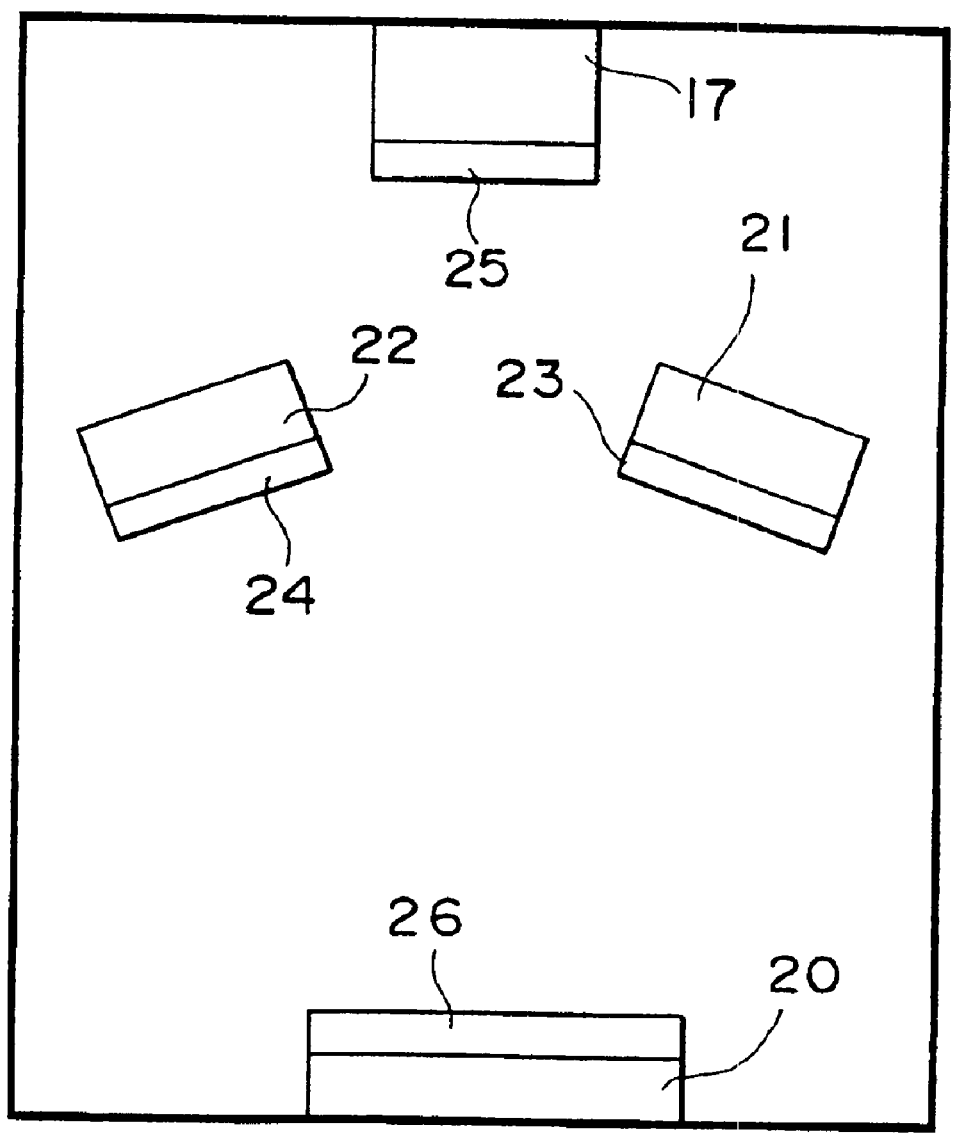
FIG. 3 is a schematic longitudinal cross sectional view showing a dark box.

FIG. 3 is a schematic vertical cross sectional view showing the dark box 2.

As shown in FIG. 3, a stage 20 is provided in the dark box 2 and a first xenon flash lamp 21 and a second xenon flash lamp 22 are disposed obliquely above the stage 20 for generating a stimulating ray whose center wavelength is 340 nm. Filters 23 and 24 are adhered to the front surfaces of the first xenon flash lamp 21 and the second xenon flash lamp 22. Each of the filters 23 and 24 has a property of cutting light components having a wavelength not close to 340 nm and harmful to the stimulation of a fluorescent dye and transmitting through only light components having a wavelength in the vicinity of 340 nm. A band-pass filter 25 for transmitting only light components having a wavelength in the vicinity of 613 nm is detachably provided on the front surface of the camera lens 17.

An image carrier 26 is placed on the stage 20 and, in this embodiment, a micro-titer plate formed with 96 wells (not shown) or a micro array is used as the image carrier 26.

Figure 4:
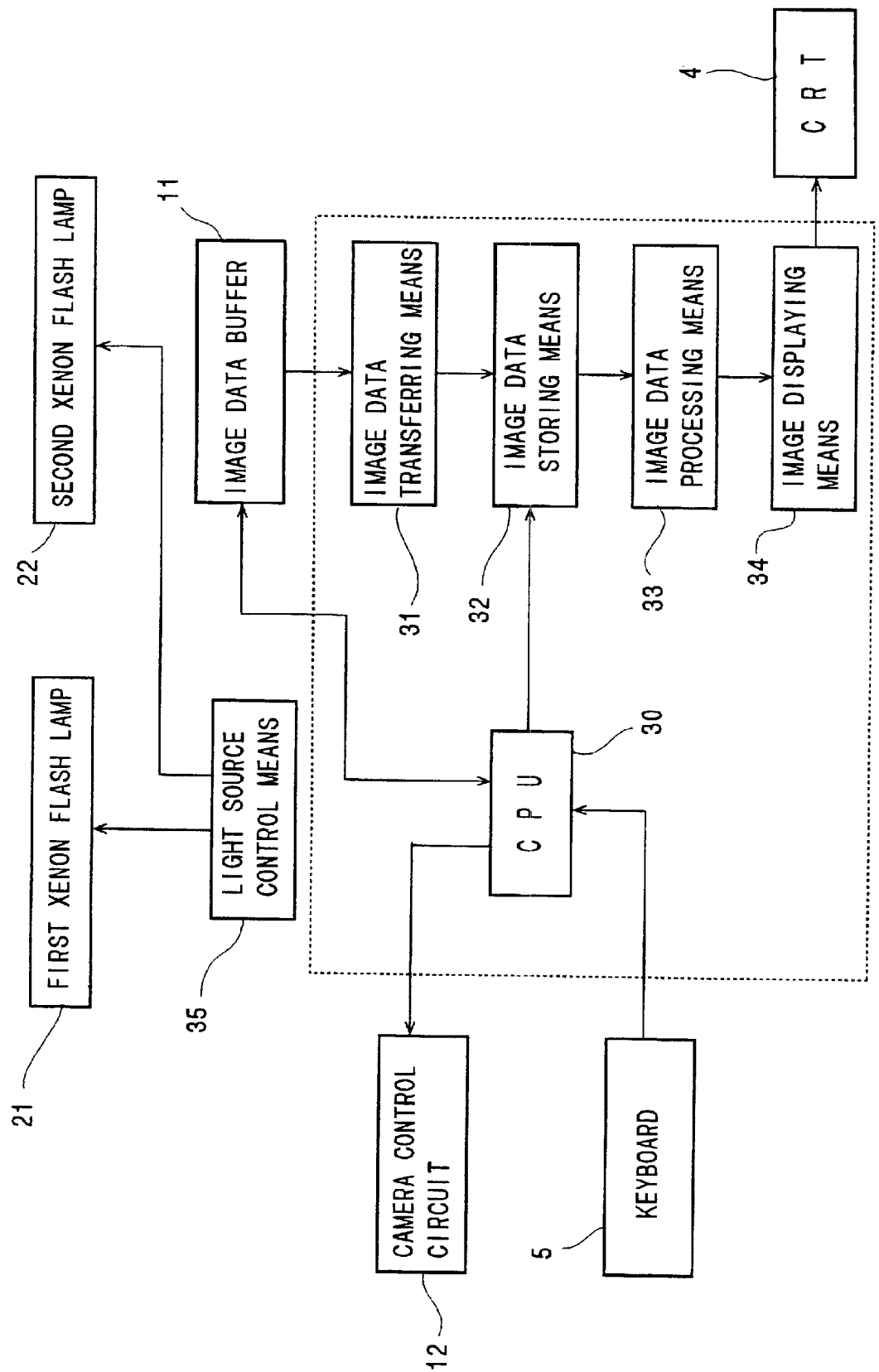
FIG. 4 is a block diagram of a personal computer and peripheral devices thereof

FIG. 4 is a block diagram of the personal computer 3 and peripheral devices thereof As shown in FIG. 4, the personal computer 3 includes a CPU 30 for controlling the exposure of the cooled CCD camera 1, an image data transferring means 31 for reading the image data produced by the cooled CCD camera 1 from the image data buffer 11, a image data storing means 32 for storing image data transferred from the image data transferring means 31, an image data processing means 33 for effecting image processing on the image data stored in the image data storing means 32, and an image displaying means 34 for displaying a visual image on the screen of the CRT 4 based on the image data stored in the image data storing means 32. The first xenon flash lamp 21 and the second xenon flash lamp 22 are controlled by a light source control means 35 and the light source control means 35 is controlled by the CPU 30. The CPU 30 is constituted so as to output various signals to the camera controlling circuit 12 of the cooled CCD camera 1.

Figure 5:
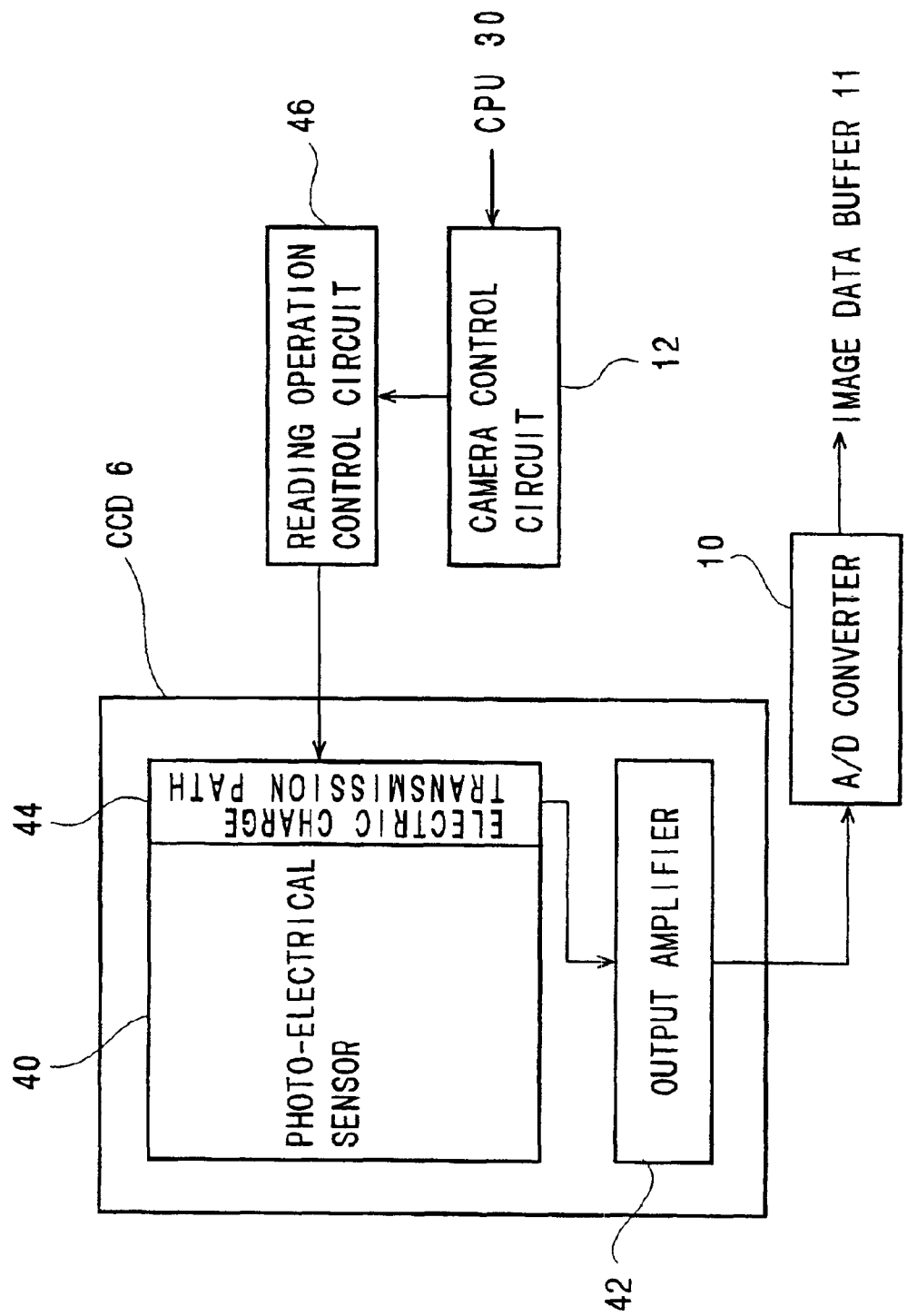
FIG. 5 is a block diagram of a CCD and peripheral devices thereof.

FIG. 5 is a block diagram of the CCD 6 and peripheral devices thereof.

As shown in FIG. 5, the CCD 6 includes a photo-electrical sensor 40 and an output amplifier 42 and electric charge stimulated in the photo-electrical sensor 40 is transmitted via an electric charge transmission path 44 to the output amplifier 42. The transmission of electric charge through the electric charge transmission path 44 is controlled by a reading operation control circuit 46 and the reading operation control circuit 46 is controlled by the camera control circuit 12.

In the image data producing apparatus according to this embodiment, a micro-titer plate formed with 96 wells (not shown) containing a specimen solution labeled with a fluorescent dye, or a micro array having spots obtained by hybridizing specific binding substances spotted on the surface of a substrate such as a slide glass plate or a membrane filter with a substance derived from a living organism and labeled with a fluorescent dye is used as an image carrier 26 and the image data producing apparatus is constituted so as to turn on the first xenon flash lamp 21 and the second xenon flash lamp 22, irradiate the image carrier 26 with a stimulating ray, thereby stimulating a fluorescent dye, turn off the first xenon flash lamp 21 and the second xenon flash lamp 22, detect residual fluorescence emission released from the fluorescent dye after the turn-off of the first xenon flash lamp 21 and the second xenon flash lamp 22 by the CCD 6 of the cooled CCD camera 1 via the camera lens 17.

When image data of a fluorescent substance carried in the micro-titer plate are to be produced, the lens focus is first adjusted by the user using the camera lens 17.

A micro-titer plate (not shown) is then placed as an image carrier 26 on the stage 20 and the dark box 2 is closed. The 96 wells of the micro-titer plate accommodate a specimen solution labeled with "DELFIA" (product name) manufactured by Wallac Oy, a business unit of PerkinElmer Life Sciences (U.S.A.), which is a fluorescent dye activated by trivalent europium.

When an exposure start signal is input by the user through the keyboard 5, the CPU 30 outputs a light source turn-on signal to the light source control means 35. When the light source control means 35 receives the light source turn-on signal, it turns on the first xenon flash lamp 21 and the second xenon flash lamp 22.

As a result, a stimulating ray whose center wavelength is 340 nm is emitted from the first xenon flash lamp 21 and the second xenon flash lamp 22 toward the image carrier 26 placed on the stage 20 and the fluorescent dye, "DELFIA" (product name) manufactured by Wallac Oy, a business unit of PerkinElmer Life Sciences (U.S.A.), labeling the specimen solution contained in the 96 wells formed in the micro-titer plate is stimulated, thereby releasing fluorescence emission having a long emission lifetime and a wavelength of 613 nm.

When a predetermined time period has passed, the CPU 30 outputs a light source turn-off signal to the light source control means 35. When the light source control means 35 receives the light source turn-off signal, it turns off the first xenon flash lamp 21 and the second xenon flash lamp 22.

At the same time, the CPU 30 outputs an exposure signal to the camera control circuit 12 of the cooled CCD camera 1, thereby causing it to open the shutter 9.

As a result, residual fluorescence emission having a wavelength of 613 nm released from the fluorescent dye even after the turn-off of the first xenon flash lamp 21 and the second xenon flash lamp 22 impinges onto the light detecting surface of the CCD 6 of the cooled CCD camera 1 via the band-pass filter 25 and the camera lens 17 to form an image on the light detecting surface. The photo-electrical sensor 40 of the CCD 6 receives light of the thus formed image and accumulates it in the form of electric charges therein. Since the band-pass filter 25 has a property of transmitting only light components having a wavelength in the vicinity of 613, the photo-electrical sensor 40 of the CCD 6 detects residual fluorescence emission having a wavelength of 613 nm and released from the fluorescent dye, "DELFIA" (product name) manufactured by Wallac Oy, a business unit of PerkinElmer Life Sciences (U.S.A.), labeling the specimen solution contained in the 96 wells formed in the micro-titer plate.

When a predetermined time period has passed, the CPU 30 outputs an exposure completion signal to the camera control circuit 12 of the cooled CCD camera 1, thereby causing it to close the shutter 9.

At the same time, the CPU 30 outputs the light-source turn-on signal to the light source control means 35, thereby causing it to turn on the first xenon flash lamp 21 and the second xenon flash lamp 22.

As a result, a stimulating ray whose center wavelength is 340 nm is again emitted from the first xenon flash lamp 21 and the second xenon flash lamp 22 toward the image carrier 26 placed on the stage 20 and the fluorescent dye, "DELFIA" (product name) manufactured by Wallac Oy, a business unit of PerkinElmer Life Sciences (U.S.A.), labeling the specimen solution contained in the 96 wells formed in the micro-titer plate is stimulated, thereby releasing fluorescence emission having a wavelength of 613 nm.

When a predetermined time period has passed, the CPU 30 outputs a light source turn-off signal to the light source control means 35. When the light source control means 35 receives the light source turn-off signal, it turns off the first xenon flash lamp 21 and the second xenon flash lamp 22.

At the same time, the CPU 30 outputs an exposure signal to the camera control circuit 12 of the cooled CCD camera 1, thereby causing it to again open the shutter 9.

As a result, long life time fluorescence emission having a wavelength of 613 nm and released from the fluorescent dye even after the turn-off of the first xenon flash lamp 21 and the second xenon flash lamp 22 impinges onto the light detecting surface of the CCD 6 of the cooled CCD camera 1 via the band-pass filter 25 and the camera lens 17 to form an image on the light detecting surface. The photo-electrical sensor 40 of the CCD 6 receives light of the thus formed image and accumulates it in the form of electric charges therein.

The on and off operations of the first xenon flash lamp 21 and the second xenon flash lamp 22 and the opening and closing operations of the shutter 9 are repeated in this manner until a predetermined exposure time period has passed.

In this embodiment, the fluorescent dye labeling the specimen solution is "DELFIA" (product name) manufactured by Wallac Oy, a business unit of PerkinElmer Life Sciences (U.S.A.), and since the decay time of residual fluorescence emission released from this fluorescent dye is about 1 millisecond, the CPU 30 is constituted so as to control the on and off operations of the first xenon flash lamp 21 and the second xenon flash lamp 22 and opening and closing operations of the shutter 9 with a frequency of 1 kHz or less.

When a predetermined exposure time has passed, the CPU 30 outputs an exposure completion signal to the light source control means 35, thereby causing it to turn off the first xenon flash lamp 21 and the second xenon flash lamp 22 and outputs the exposure completion signal to the camera control circuit 12 of the cooled CCD camera 1.

When the camera control circuit 12 receives the exposure completion signal from the CPU 30, it drives the reading operation control circuit 46, thereby causing it to transmit analog image data accumulated in the form of electric charge by the photo-electrical sensor 40 of the CCD 6 to the output amplifier 42 via the electric charge transmission path 44 and further transfer them to the A/D converter 10. The image data is digitized by the A/D converter 10 and temporarily stored in the image data buffer 11.

At the same time the CPU outputs the exposure completion signal to the camera control circuit 12, it outputs a data transfer signal to the image data transferring means 31, thereby causing it to read image data from the image data buffer 11 of the cooled CCD camera 1 and store them in the image data storing means 32.

When the user inputs an image producing signal through the keyboard 5, image data stored in the image data storing means 32 are read by the image display means 34 and are subjected to image data processing by the image data processing means 33 as occasion demands and an image of a fluorescent dye labeling the specimen solution contained in the 96 wells of the micro-titer plate is displayed on the screen of the CRT 4 based on the thus processed image data.

When image data of a fluorescent dye carried in a micro array are to be produced, a micro array having spots obtained by hybridizing specific binding substances spotted on the surface of a substrate such as a slide glass plate or a membrane filter with a substance derived from a living organism and labeled with a fluorescent dye is placed as an image carrier on the stage 20 and the dark box 2 is closed.

Similarly to the production of image data from the micro-titer plate, on and off operations of the first xenon flash lamp 21 and the second xenon flash lamp 22 and opening and closing operations of the shutter 9 are controlled by the CPU 30 with a frequency of 1 kHz or less. When a predetermined exposure time has passed, analog data accumulated in the form of electric charge by the photo-electrical sensor 40 of the CCD 6 are transmitted to the A/D converter 10 via the electric charge transmission path 44 and the output amplifier 42 and digitized by the A/D converter 10 to produce digital image data.

Similarly to the production of the image from the micro-titer plate, based on the thus produced digital image data, an image of a fluorescent dye labeling a substance derived from a living organism hybridized with a specific binding substance spotted on the surface of a substrate such as a slide glass plate or a membrane filter is displayed on the screen of the CRT 4.

According to the above described embodiment, while the shutter 9 is kept closed, a fluorescent dye labeling the specimen solution contained in the 96 wells of the micro-titer plate or a fluorescent dye labeling a substance derived from a living organism hybridized with a specific binding substance spotted on the surface of a substrate such as a slide glass plate or a membrane filter is excited by turning on the first xenon flash lamp 21 and the second xenon flash lamp 22 and image data are produced by turning off the first xenon flash lamp 21 and the second xenon flash lamp 22, opening the shutter 9 and photoelectrically detecting residual fluorescence emission released from the fluorescent dye after the turn-off of the first xenon flash lamp 21 and the second xenon flash lamp 22 by the photo-electrical sensor 40 of the CCD 6. Therefore, since the first xenon flash lamp 21 and the second xenon flash lamp 22 are held off when the residual fluorescence emission is detected by the cooled CCD camera 1, it is possible to markedly lower noise in image data caused by detecting a stimulating ray emitted from the first xenon flash lamp 21 and the second xenon flash lamp 22 by the photo-electrical sensor 40 of the CCD 6.

Further, according to the above described embodiment, image data of the fluorescent dye labeling the specimen solution contained in all of the 96 wells of the micro-titer plate or image data of the fluorescent dye contained in all of the spots and labeling a substance derived from a living organism hybridized with a specific binding substance spotted on the surface of a substrate such as a slide glass plate or a membrane filter are produced by the cooled CCD camera 1 at the same time. Therefore, even in the case where the reaction of the specimen solution in the wells formed in the micro-titer plate progresses with the elapse of time, image data with markedly low noise can be produced rapidly with a simple operation because the specimen solution labeled with a fluorescent dye can be simultaneously poured into all of the 96 wells formed in the micro-titer plate. Moreover, even in the case where the state of the spots formed by hybridizing a substance derived from a living organism and labeled with a labeling substance with a specific binding substance spotted on the surface of a substrate such as a slide glass plate or a membrane filter changes with the elapse of time, image data can be produced without being affected by the elapse of time.

Furthermore, according to the above described embodiment, since the on and off operations of the first xenon flash lamp 21 and the second xenon flash lamp 22 and the opening and closing operations of the shutter 9 are controlled with a frequency of 1 kHz or less until a predetermined exposure time has passed, the photo-electrical sensor 40 of the CCD 6 of the cooled CCD camera 1 can detect a sufficient amount of residual fluorescence emission and, therefore, it is possible to produce image data based on which a desired image can be generated.

Figure 6:
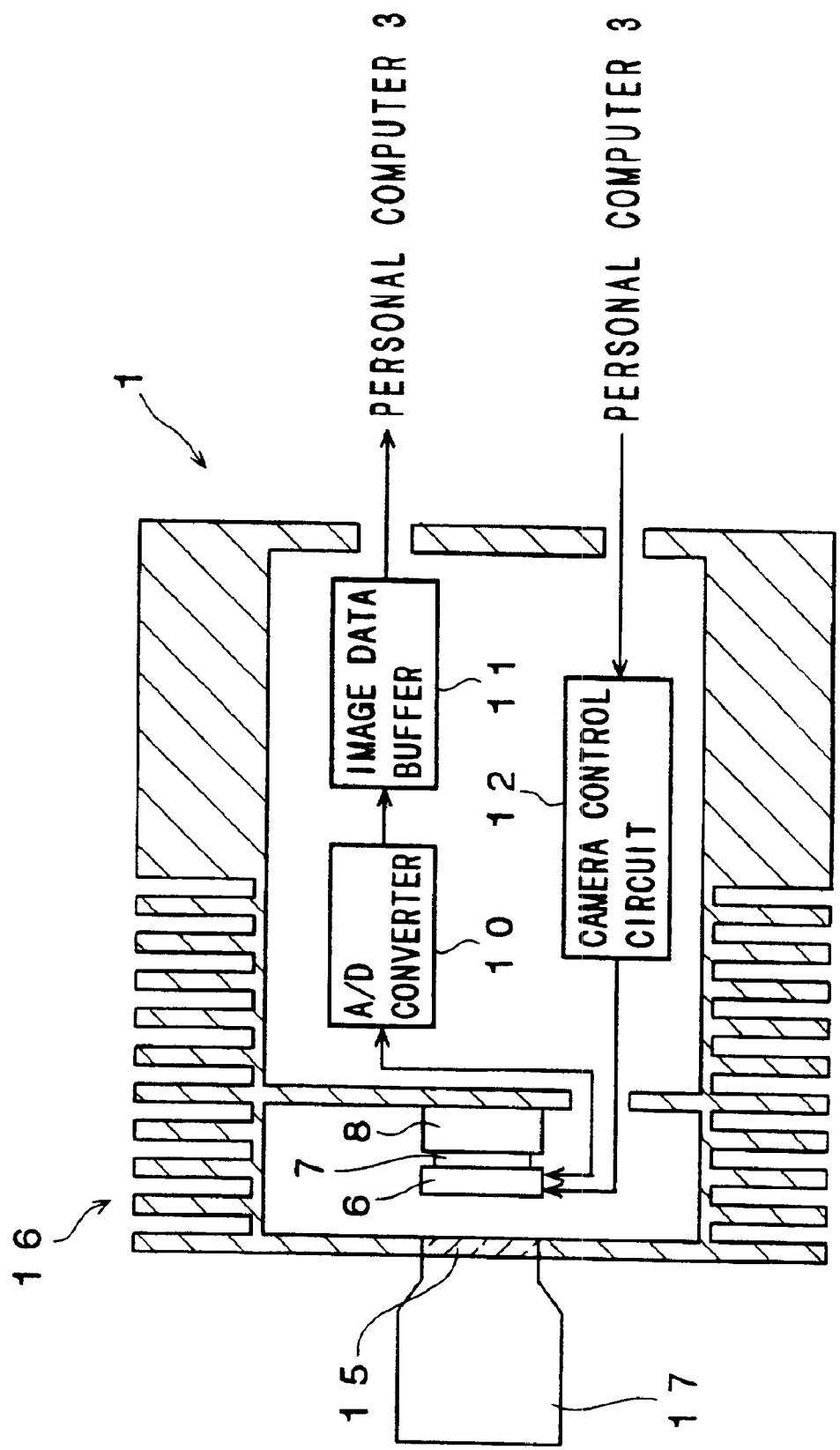
FIG. 6 is a schematic cross sectional view showing a cooled CCD camera of an image data producing apparatus which is another preferred embodiment of the present invention.

FIG. 6 is a schematic cross sectional view showing a cooled CCD camera of an image data producing apparatus which is another preferred embodiment of the present invention.

As shown in FIG. 6, in the image data producing apparatus according to this embodiment, the cooled CCD camera 1 has the same configuration as that of the cooled CCD camera shown in FIG. 2 except that it is not provided with any shutter.

Figure 7:
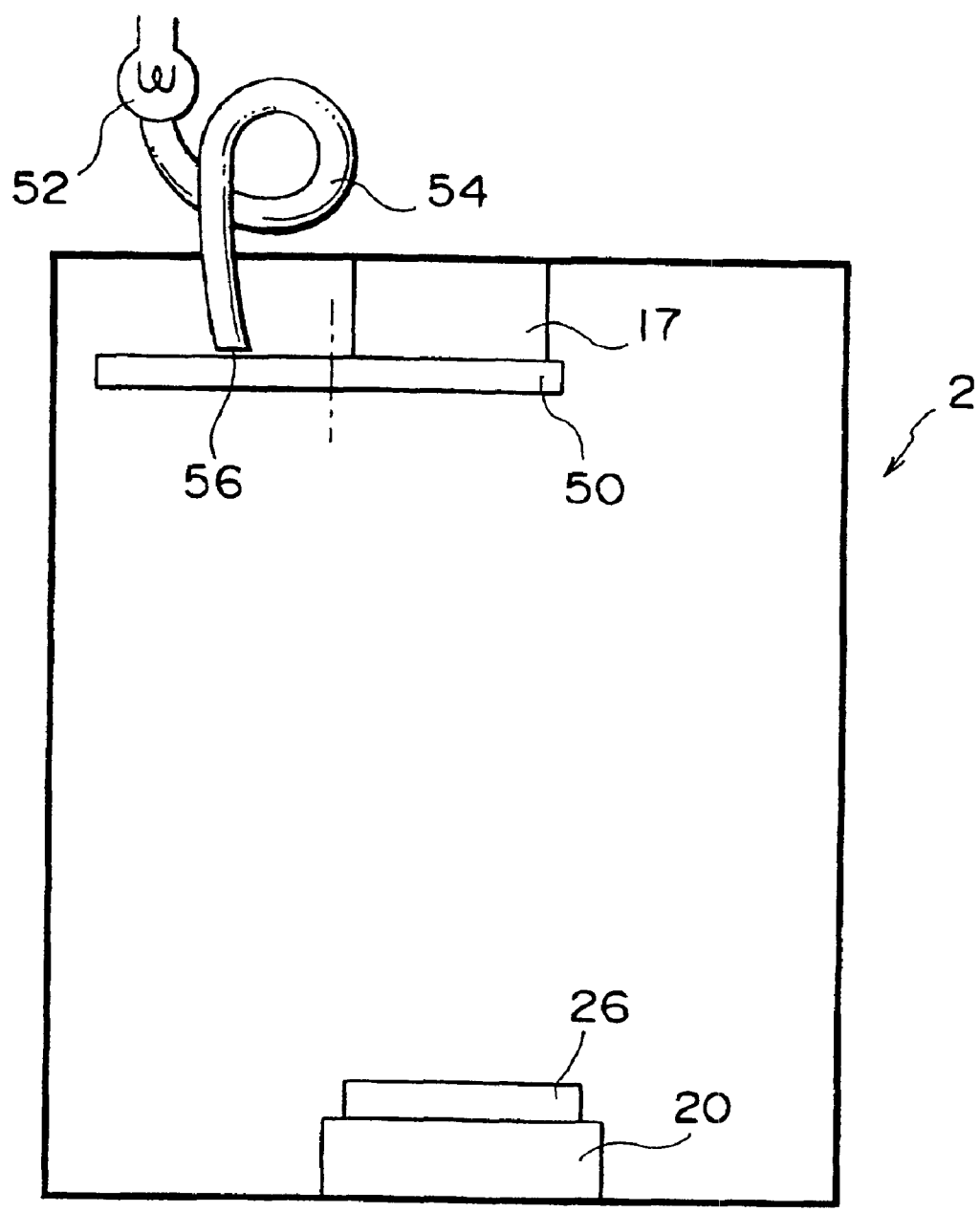
FIG. 7 is a schematic longitudinal cross sectional view showing a dark box of an image data producing apparatus which is another preferred embodiment of the present invention.

FIG. 7 is a schematic cross sectional view showing a dark box 2.

As shown in FIG. 7, the image data producing apparatus according to this embodiment is not provided with a band-pass filter for transmitting only light having a wavelength in the vicinity of 613 nm and a stimulating ray emitted from a xenon flash lamp 52 is led by an optical fiber bundle 54 into the dark box 2.

As shown in FIG. 7, a chopper 50 is disposed in front of the camera lens 17 of the cooled CCD camera 1 and the stimulating ray emitting end portion 56 of the optical fiber bundle 54.

Figure 8:
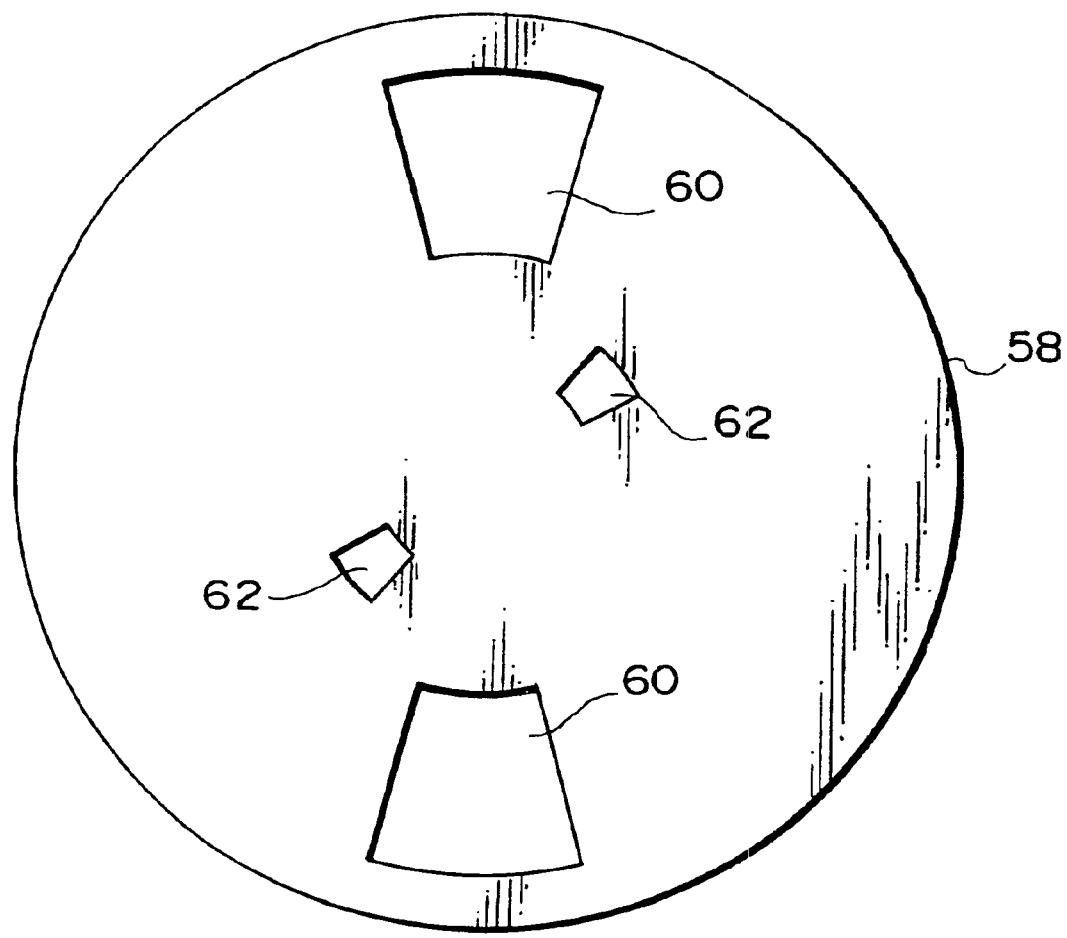
FIG. 8 is a schematic plan view showing a chopper.

FIG. 8 is a schematic plan view showing the chopper 50.

As shown in FIG. 8, the chopper 50 is formed of a rotatable disk 58 and the disk 58 is formed with a pair of CCD exposure openings 60 for exposing CCD 6 angularly spaced apart by 180 degrees from each other and a pair of stimulating ray lead openings 62 angularly spaced apart by 180 degrees from each other.

In this embodiment, the pair of CCD exposure openings 60 and the pair of stimulating ray lead openings 62 are formed in such a positional relationship that when one of the CCD exposure openings 60 is located in front of the camera lens 17 of the cooled CCD camera 1, the stimulating ray lead openings 62 are retracted from the front portion of the stimulating ray emitting end portion 56 of the optical fiber bundle 54 and the stimulating ray emitting end portion 56 of the optical fiber bundle 54 is closed by the disk 58 of the chopper 50 and that when one of the stimulating ray lead openings 62 is located in front of the stimulating ray emitting end portion 56 of the optical fiber bundle 54, the CCD exposure openings 60 are retracted from the front portion of the camera lens 17 of the cooled CCD camera 1 and the camera lens 17 is closed by the disk 58 of the chopper 50.

In this embodiment, the rotation of the chopper 50 is controlled by the CPU 30 of the personal computer 3.

In this embodiment, "DELFIA" (product name) manufactured by Wallac Oy, a business unit of PerkinElmer Life Sciences (U.S.A.), is used as a fluorescent substance labeling a specimen solution contained in 96 wells formed in a micro-titer plate or a fluorescent substance labeling a substance derived from a living organism and hybridized with a specific binding substance spotted on the surface of a substrate such as a slide glass plate or a membrane filter and since the decay time of residual fluorescence emission released from this fluorescent substance is about 1 millisecond, the CPU 30 is constituted so as to control the on and off operations of the xenon flash lamp 52 with a frequency of 1 kHz or less. For example, when the xenon flash lamp 52 is driven with a frequency of 100 Hz, the CPU 30 controls a motor (not shown) for rotating the chopper 50 so that the chopper 50 is rotated at 3000 rpm during the exposure of the CCD 6.

The thus constituted image data producing apparatus according to this embodiment of the present invention produces image data of a fluorescent substance carried in a micro-titer plate as follows.

The lens focus is first adjusted by the user using the camera lens 17 while one of the CCD exposure openings 60 of the chopper 50 is held in front of the camera lens 17.

A micro-titer plate (not shown) is then placed as an image carrier 26 on the stage 20 and the dark box 2 is closed. The 96 wells of the micro-titer plate hold a specimen solution labeled with "DELFIA" (product name) manufactured by Wallac Oy, a business unit of PerkinElmer Life Sciences (U.S.A.), which is a fluorescent dye activated by trivalent europium.

When an exposure start signal is input through the keyboard 5 by the user, the CPU 30 outputs a drive signal to a motor (not shown) for rotating the chopper 50, thereby rotating the chopper 50 so that the on and off operations of the xenon flash lamp 52 can be controlled with a frequency of 1 kHz or less. For example, when the xenon flash lamp 52 is driven with a frequency of 100 Hz, the CPU 30 controls the motor for rotating the chopper 50 so that the chopper 50 is rotated at 3000 rpm. during the exposure of the CCD 6.

The CPU 30 then outputs a light source turn-on signal to the light source control means 35 and when the light source control means 35 receives the light source turn-on signal, it turns on the xenon flash lamp 52.

As a result, since the pair of CCD exposure openings 60 and the pair of stimulating ray lead openings 62 are formed in the disk 58 in such a positional relationship that when one of the stimulating ray lead openings 62 is located in front of the stimulating ray emitting end portion 56 of the optical fiber bundle 54, the CCD exposure openings 60 are retracted from the front portion of the camera lens 17 of the cooled CCD camera 1 and the camera lens 17 is closed by the disk 58 of the chopper 50, while the camera lens 17 is closed by the disk 58 of the chopper 50, a stimulating ray whose center wavelength is 340 nm emitted from the xenon flash lamp 52 is led into the dark box 2 via the the stimulating ray emitting end portion 56 of the optical fiber bundle 54 and "DELFIA" (product name) manufactured by Wallac Oy, a business unit of PerkinElmer Life Sciences (U.S.A.), the fluorescent substance labeling the specimen solution contained in the 96 wells formed in the micro-titer plate, releases fluorescence emission having a wavelength of 613 nm.

On the other hand, since when one of the CCD exposure openings 60 is located in front of the camera lens 17 of the cooled CCD camera 1, the stimulating ray lead openings 62 are retracted from the front portion of the stimulating ray emitting end portion 56 of the optical fiber bundle 54 and the stimulating ray emitting end portion 56 of the optical fiber bundle 54 is closed by the disk 58 of the chopper 50, only when a stimulating ray emitted from the xenon flash lamp 52 is not led into the dark box 2 by the stimulating ray emitting end portion 56 of the optical fiber bundle 54, residual fluorescence emission having a wavelength of 613 nm released from the fluorescent substance after the completion of the irradiation with the stimulating ray impinges on the light detecting surface of the CCD 6 of the cooled CCD camera 1 via the camera lens 17 to form an image on the light detecting surface and the photo-electrical sensor 40 of the CCD 6 receives light of the thus formed image and accumulates it in the form of electric charges therein.

During the exposure of the CCD 6, the chopper 50 is rotated by the CPU 30 so that the on and off operations of the xenon flash lamp are controlled with a frequency of 1 kHz or less; for example, the chopper 50 is driven with a frequency of 100 Hz to rotate the chopper 50 at 3000 rpm. The irradiation of the fluorescent substance with the stimulating ray and the detection of residual fluorescence emission are therefore repeated with a frequency of 1 kHz or less.

When a predetermined exposure time has passed, the CPU 30 outputs an exposure completion signal to the light source control means 35, thereby causing it to turn off the xenon flash lamp 52 and outputs the exposure completion signal to the camera control circuit 12 of the cooled CCD camera 1.

When the camera control circuit 12 receives the exposure completion signal from the CPU 30, it drives the reading operation control circuit 46, thereby causing it to transmit analog image data accumulated by the photo-electrical sensor 40 of the CCD 6 in the form of electric charge to the output amplifier 42 via the electric charge transmission path 44 and transfer them to the A/D converter 10. The image data are digitized by the A/D converter 10 and temporarily stored in the image data buffer 11.

At the same time the CPU 30 outputs the exposure completion signal to the camera control circuit 12, the CPU 30 outputs a data transfer signal to the image data transferring means 31, thereby causing it to read image data from the image data buffer 11 of the cooled CCD camera 1 and store them in the image data storing means 32.

When the user inputs an image producing signal through the keyboard 5, image data stored in the image data storing means 32 are read by the image display means 34 and are subjected to image data processing by the image data processing means 33 as occasion demands and an image of a fluorescent dye labeling the specimen solution contained in the 96 wells of the micro-titer plate is displayed on the screen of the CRT 4 based on the thus processed image data.

When image data of a fluorescent dye carried in a micro array are to be produced, similarly to the above, the chopper 50 is rotated so that the on and off operations of the xenon flash lamp 52 are controlled with a frequency of 1 kHz or less, for example, the chopper 50 is rotated at 3000 rpm during the exposure of the CCD 6 when the chopper 50 is driven with a frequency of 100 Hz, and residual fluorescence emission is detected by the cooled CCD camera 1.

According to this embodiment, since the irradiation of the fluorescent substance with the stimulating ray and the detection of residual fluorescence emission are repeated by rotating the chopper 50, only when the image carrier 26 is not irradiated with a stimulating ray, residual fluorescence emission can be reliably detected by the photo-electrical sensor 40 of the CCD 6 with a simple configuration and, therefore, it is possible to markedly reduce noise in image data caused by detecting a stimulating ray emitted from the xenon flash lamp 52 by the photo-electrical sensor 40 of the CCD 6.

Further, according to this embodiment, since no band-pass filter for transmitting only light components having a wavelength in the vicinity of 613 nm is provided in front of the camera lens 17, a greater amount of residual fluorescence emission can be detected by the photo-electrical sensor 40 of the CCD 6.

Figure 9:
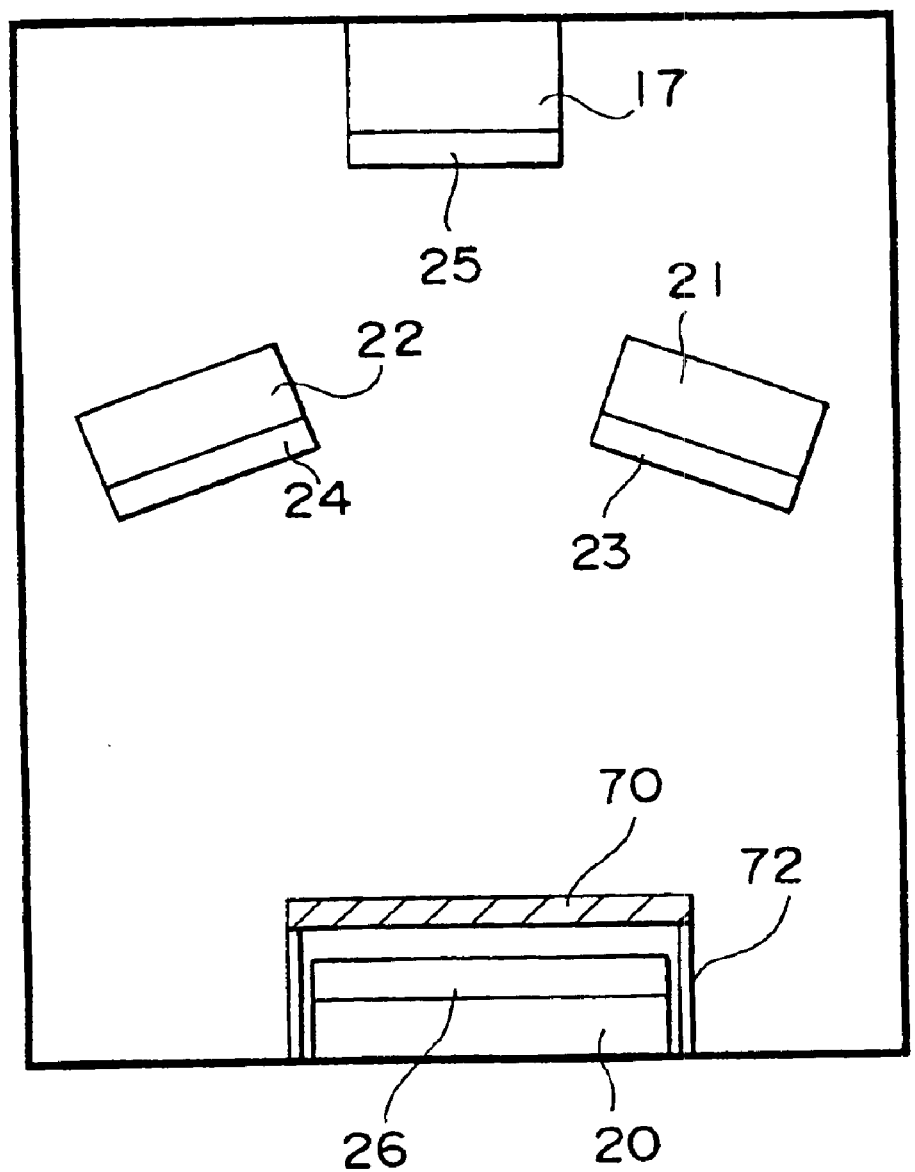
FIG. 9 is a schematic longitudinal cross sectional view showing a dark box of an image data producing apparatus which is a further preferred embodiment of the present invention.

FIG. 9 is a schematic longitudinal cross sectional view showing a dark box 2 of an image data producing apparatus which is a further preferred embodiment of the present invention.

As shown in FIG. 9, the image data producing apparatus according to this embodiment has the same configuration as that of the image data producing apparatus according to the embodiment shown in FIGS. 1 to 5 except that it further includes a Fresnel lens 70 supported by a stay 72 above the stage 20.

In this embodiment, since the image data producing apparatus further includes the Fresnel lens 72 above the stage 20, in the case where an image of a fluorescent dye labeling a specimen solution contained in 96 wells of a micro-titer plate is read, fluorescence emission released from the micro-titer plate can be detected by the photo-electrical sensor 40 of the CCD 6 without parallax and image data can be produced.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, "DELFIA" (product name) manufactured by Wallac Oy, a business unit of PerkinElmer Life Sciences (U.S.A.), is used as a fluorescent substance labeling a specimen solution contained in 96 wells formed in a micro-titer plate or a fluorescent substance labeling a substance derived from a living organism and hybridized with a specific binding substance spotted on the surface of a substrate such as a slide glass plate or a membrane filter. However, any fluorescent substance which can release fluorescence emission having a long emission lifetime whose decay time is longer than a predetermined length, may be used and instead of "DELFIA" (product name). Specifically, a fluorescent dye such as "SYPRO RUBY" (registered trademark) may be employed.

Further, in the above described embodiments, although a micro-titer plate formed with 96 wells is used, a micro-titer plate formed with, for instance, 384 wells may be used and the number of wells formed in a micro-titer plate is in no way limited.

Furthermore, in the above described embodiments, although the CPU 30 controls the on and off operations of the first xenon flash lamp 21 and the second xenon flash lamp 22 and the opening and closing operations of the shutter 9 or the rotation of the chopper 50 so that the irradiation of the fluorescent substance with the stimulating ray and the detection of residual fluorescence emission are repeated with a frequency of 1 kHz or less, the frequency with which the repetition of the irradiation of the fluorescent substance with the stimulating ray and the detection of residual fluorescence emission is controlled can be arbitrarily determined based upon the decay time of residual fluorescence emission released from the fluorescent substance.

Moreover, in the above described embodiments, although the first xenon flash lamp 21 and the second xenon flash lamp 22, or the xenon flash lamp 52 is used for generating a stimulating ray whose center wavelength is 340 nm, the stimulating ray source is not limited to that for emitting a stimulating ray having such a wavelength and an arbitrary stimulating ray source may be adopted based on upon the fluorescent substance used.

Further, in the embodiment shown in FIGS. 1 to 5 and the embodiment shown in FIG. 9, although the band-pass filter 25 for transmitting only light components having a wavelength in the vicinity of 613 nm is provided in front of the camera lens 17, instead of the band-pass filter 25 for transmitting only light components having a wavelength in the vicinity of 613 nm, there can be provided a stimulating ray cut filter for cutting light components having a wavelength close to that of the stimulating ray.

Furthermore, in the embodiment shown in FIGS. 6 to 8, although no band-pass filter is provided in front of the camera lens 17, a band-pass filter for transmitting only light components having a wavelength in the vicinity of 613 nm may be provided in front of the camera lens 17.

Moreover, in the embodiment shown in FIGS. 1 to 5 and the embodiment shown in FIG. 9, although the band-pass filter 25 for transmitting only light components having a wavelength in the vicinity of 613 nm is provided in front of the camera lens 17, the band-pass filter may be omitted.

Further, in the embodiment shown in FIGS. 1 to 5, although both the first xenon flash lamp 21 and the second xenon flash lamp 22 are provided, only one of them may be provided.

Furthermore, in the embodiment shown in FIGS. 6 to 8, although a single xenon flash lamp 52 is provided, two xenon flash lamps may be provided so as to be located on the opposite sides of the camera lens 17.

Moreover, in the embodiment shown in FIGS. 6 to 8, although no Fresnel lens is provided, similarly to the embodiment shown in FIG. 9, a Fresnel lens 70 may be provided.

Further, in the embodiment shown in FIG. 9, although the Fresnel lens 70 is supported by the stay 72, it may be superposed on the micro-titer plate.

Furthermore, in the embodiment shown in FIG. 9, although the Fresnel lens 70 is provided, instead of the Fresnel lens, a convex lens may be provided.

Moreover, the above described embodiments were explained with regard to the production of image data by reading an image of a fluorescent dye labeling a specimen solution contained in 96 wells formed in a micro-titer plate or an image of a fluorescent dye labeling a substance derived from a living organism and hybridized with a specific binding substance spotted on the surface of a substrate such as a slide glass plate or a membrane filter. However, the present invention is in no way limited to the production of image data by reading an image of a fluorescent dye but can be widely applied to reading and production of an image of a fluorescent substance in a state labeling two-dimensionally distributed specimen spots.

Further, in the above described embodiments, although the periphery of the cooled CCD camera 1 is formed with heat dispersion fins 16 over substantially half its length for dispersing heat, the heat dispersion fins 16 may be formed over the entire length of the periphery of the cooled CCD camera 1 and how dispersion fins are formed on the periphery of the cooled CCD camera 1 can be arbitrarily determined.

Furthermore, in the above described embodiments, although the cooled CCD camera 1 is used, it is possible to use a CCD camera provided with no cooling means.

Moreover, in the above described embodiments, although the CCD camera 1 is used, instead of the CCD camera 1, some other solid state imaging device such as a CID (Charge Injection Device), a PDA (Photo-Diode Array), a MOS type imaging device or the like which can serve as a two dimensional area sensor may be employed.

Further, in the embodiment shown in FIGS. 6 to 8, although the chopper 50 formed with a pair of CCD exposure openings 60 and a pair of stimulating ray lead openings 62 is used, it is possible to use a chopper 50 formed with one CCD exposure opening 60 and one stimulating ray lead opening 62 or a chopper 50 formed with three or more CCD exposure openings 60 and three or more stimulating ray lead openings 62.

Furthermore, in the embodiment shown in FIGS. 6 to 8, although the stimulating ray emitted from the xenon flash lamp 52 is led by the optical fiber bundle 54, instead of the optical fiber bundle 54, other light guide may be employed.

Moreover, in the embodiment shown in FIGS. 6 to 8, although the chopper 50 is disposed in front of the stimulating ray emitting end portion 56 of the optical fiber bundle 54 for leading the stimulating ray emitted from the xenon flash lamp 52, the chopper 50 can be disposed in front of the xenon flash lamp 52 without providing the optical fiber bundle 54.

Further, in the above described embodiments, although an image is reproduced on the screen of the CRT 4, instead of a CRT 4, a flat display panel such as a liquid crystal display, an organic EL display or the like may be used.

According to the present invention, it is possible to provide an image data producing method and apparatus which can produce low-noise image data rapidly with a simple operation by irradiating an image carrier including independently formed and two-dimensionally distributed specimen spots, at least some of which contain a fluorescent substance, with a stimulating ray to excite the fluorescent substance and photoelectrically detecting fluorescence emission released from the fluorescent substance.

What is claimed is:

1. An image data producing method comprising:
   at same time irradiating an entire image carrier comprising independently formed and two-dimensionally distributed specimen spots, at least one specimen spot containing a fluorescent substance, with a stimulating ray to excite the fluorescent substance contained in the specimens;
   stopping the irradiation of the image carrier with the stimulating ray, and
   photoelectrically detecting residual fluorescence emission released from the fluorescent substance contained in the specimens after stopping the irradiation with the stimulating ray using a two-dimensional area sensor.

2. An image data producing method in accordance with claim 1, wherein the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are repeated two or more times.

3. An image data producing method in accordance with claim 1, wherein the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on and off operations of at least one stimulating ray source for emitting a stimulating ray and opening and closing operations of a shutter of the two-dimensional area sensor.

4. An image data producing method in accordance with claim 1, wherein the steps of irradiating the image carrier with the stimulating ray to excite the fluorescent substance contained in the specimens, stopping the irradiation of the image carrier with the stimulating ray, and photoelectrically detecting residual fluorescence emission released from the fluorescent substance contained in the specimens after stopping the irradiation with the stimulating ray using the two-dimensional area sensor are performed by synchronizing on-off operations of at least one stimulating ray source for emitting a stimulating ray and opening and closing operations of a shutter of the two-dimensional area sensor using a chopper.

5. An image data producing method in accordance with claim 1, wherein image data are produced by detecting residual fluorescence emission by the two-dimensional area sensor via a filter for cutting at least light having a wavelength of the stimulating ray.

6. An image data producing method in accordance with claim 1 wherein image data are produced by detecting residual fluorescence emission by the two-dimensional area sensor via a Fresnel lens.

7. An image data producing method in accordance with claim 1, wherein image data are produced by using a CCD camera as the two-dimensional area sensor.

8. An image data producing method in accordance with claim 7, wherein image data are produced by using a cooled CCD camera as the two-dimensional area sensor.

9. An image data producing method in accordance with claim 1, wherein a micro-titer plate formed with numerous wells holding specimens labeled with a fluorescent dye is used as the image carrier.

10. A method according to claim 1, wherein the stimulating ray emits light to the entire image carrier simultaneously.

11. A method according to claim 10, wherein the fluorescent substance has a decay time of approximately 1 millisecond.

12. A method according to claim 10, wherein the area sensor comprises a CCD array receiving fluorescent emissions from all fluorescent containing specimens excited by said stimulating ray simultaneously.

13. A method according to claim 1, wherein the stimulating ray is controlled with a frequency of 1 KHz or less.

14. An image data producing apparatus comprising at least one stimulating ray source for emitting a stimulating ray, a stage on which an image carrier including independently formed and two-dimensionally distributed specimen spots, at least some of which contain a fluorescent substance, is to be placed, a two-dimensional area sensor, and a control means for irradiating at same time the entire image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens.

15. An image data producing apparatus in accordance with claim 14 wherein the control means is constituted so as to repeat the steps of irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens two or more times.

16. An image data producing apparatus in accordance with claim 14, wherein the control means is constituted so as to synchronize on and off operations of at least one stimulating ray source and opening and closing operations of a shutter of the two-dimensional area sensor in such a manner that the shutter of the two-dimensional area sensor is closed when the at least one stimulating ray source is held on and it is opened only when the at least one stimulating ray source is held off, thereby irradiating the image carrier placed on the stage with a stimulating ray emitted from the at least one stimulating ray source to excite a fluorescent substance contained in the specimens, stopping the irradiation with the stimulating ray and causing the two-dimensional area sensor to photoelectrically detect residual fluorescence emission released from the fluorescent substance contained in the specimens.

17. An image data producing apparatus in accordance with claim 14, which further comprises a filter for cutting at least light having a wavelength of the stimulating ray.

18. An image data producing apparatus in accordance with claim 14, which further comprises a Fresnel lens between the stage and the two-dimensional area sensor.

19. An image data producing apparatus in accordance with claim 14, wherein the two-dimensional area sensor is constituted as a CCD camera.

20. An image data producing apparatus in accordance with claim 19, wherein the two-dimensional area sensor is constituted as a cooled CCD camera.

21. An image data producing apparatus in accordance with claim 14, wherein the image carrier is constituted by a micro-titer plate formed with numerous wells holding specimens labeled with a fluorescent dye.

22. An image data producing apparatus comprising:
at least one stimulating ray source for emitting a stimulating ray,
a stage on which an image carrier including independently formed and two-dimensionally distributed specimen spots, at least some of which contain a fluorescent substance, is to be placed,
a two-dimensional area sensor,
a control means for irradiating the image carrier placed on the stage with a stimulating ray emitted from the at least one stimulating ray source, thereby exciting a fluorescent substance contained in the specimens, stopping the irradiation with the stimulating ray and causing the two-dimensional area sensor to photoelectrically detect residual fluorescence emission released from the fluorescent substance contained in the specimens and
a disk-like rotatable chopper having at least two openings,
wherein the control means is constituted so as to control the rotation of the chopper in such a manner that a light detecting surface of the two-dimensional area sensor is covered by the chopper when one of the openings of the chopper is located in an optical path of the stimulating ray emitted from the at least one stimulating ray source and one of the openings of the chopper is located in front of the light detecting surface of the two-dimensional area sensor only when the chopper is located in the optical path of the stimulating ray emitted from the at least one stimulating ray source to cut the stimulating ray.

23. An image data producing apparatus in accordance with claim 22, which further comprises a light guide for leading a stimulating ray emitted from the at least one stimulating ray source and the control means is constituted so as to control the rotation of the chopper in such a manner that a light detecting surface of the two-dimensional area sensor is covered by the chopper when one of the openings of the chopper is located in front of a stimulating ray emitting end portion of the light guide and one of the openings of the chopper is located in front of the light detecting surface of the two-dimensional area sensor only when the chopper is located in front of the stimulating ray emitting end portion of the light guide to cut the stimulating ray.

24. An image data producing apparatus in accordance with claim 23, wherein the light guide is constituted by an optical fiber bundle.

25. An image data producing apparatus in accordance with claim 22, wherein the chopper is formed with four openings.

* * * * *